(12) United States Patent
Ueda et al.

(10) Patent No.: US 6,589,566 B2
(45) Date of Patent: Jul. 8, 2003

(54) COMPOSITION COMPRISING THEANINE

(76) Inventors: Tomoko Ueda, c/o Taiyo Kagaku Co., Ltd., 9-5, Akahorishinmachi, Yokkaichi-shi, Mie 510-0825 (JP); Yukiko Nagato, c/o Taiyo Kagaku Co., Ltd., 9-5, Akahorishinmachi, Yokkaichi-shi, Mie 510-0825 (JP); Yukiko Tanaka, c/o Taiyo Kagaku Co., Ltd., 9-5, Akahorishinmachi, Yokkaichi-shi, Mie 510-0825 (JP); Tsutomu Okubo, c/o Taiyo Kagaku Co., Ltd., 9-5, Akahorishinmachi, Yokkaichi-shi, Mie 510-0825 (JP); Kanari Kobayashi, c/o Taiyo Kagaku Co., Ltd., 9-5, Akahorishinmachi, Yokkaichi-shi, Mie 510-0825 (JP); Nobuyuki Aoi, c/o Taiyo Kagaku Co., Ltd., 9-5, Akahorishinmachi, Yokkaichi-shi, Mie 510-0825 (JP); Seiji Shu, c/o Taiyo Kagaku Co., Ltd., 9-5, Akahorishinmachi, Yokkaichi-shi, Mie 510-0825 (JP); Lekh Raj Juneja, c/o Taiyo Kagaku Co., Ltd., 9-5, Akahorishinmachi, Yokkaichi-shi, Mie 510-0825 (JP)

(*) Notice: Subject to any disclaimer, the term of this patent is extended or adjusted under 35 U.S.C. 154(b) by 0 days.

(21) Appl. No.: 09/757,586

(22) Filed: Jan. 11, 2001

(65) Prior Publication Data

US 2001/0001307 A1 May 17, 2001

Related U.S. Application Data

(62) Division of application No. 09/655,336, filed on Sep. 5, 2000, which is a division of application No. 09/403,486, filed as application No. PCT/JP99/00784 on Feb. 23, 1999.

(30) Foreign Application Priority Data

| Feb. 23, 1998 | (JP) | 10-57470 |
|---|---|---|
| May 8, 1998 | (JP) | 10-142119 |
| Aug. 6, 1998 | (JP) | 10-234968 |
| Nov. 5, 1998 | (JP) | 10-330207 |

(51) Int. Cl.$^7$ .............. A61K 33/34; A61K 33/32; A61K 33/26; A61K 33/14; A61K 31/195
(52) U.S. Cl. .............. 424/617; 424/630; 424/639; 424/641; 424/646; 424/677; 424/702; 514/563
(58) Field of Search ............ 424/617, 630, 424/638, 639, 640, 641, 677, 702, 646; 514/563

(56) References Cited

U.S. PATENT DOCUMENTS

| 5,071,653 A | 12/1991 | Kakuda et al. |
|---|---|---|
| 5,501,866 A | 3/1996 | Kakuda et al. |
| 5,736,575 A | 4/1998 | Kakuda et al. |
| 6,063,428 A * | 5/2000 | Ekanayake et al. ......... 426/597 |

FOREIGN PATENT DOCUMENTS

| AU | 4281397 | 6/1998 |
|---|---|---|
| EP | 0 845 264 A1 | 6/1998 |
| JP | A6-40901 | 2/1994 |
| JP | A6-100442 | 4/1994 |

OTHER PUBLICATIONS

Database WPI, Section Ch, Week 199725 Derwent Publications Ltd., London, GB; An 1997–276683 XP002196618, & JP 09 100230 A (Itoen KK), Apr. 15, 1997 *abstract*.

(List continued on next page.)

*Primary Examiner*—Russell Travers
*Assistant Examiner*—Shengjun Wang

(57) ABSTRACT

The present invention relates to a composition for suppressing or ameliorating a symptom accompanying diminished homeostasis, comprising theanine; and a mineral composition comprising theanine and a mineral. According to the present invention, there can be provided a composition for suppressing or ameliorating the above symptoms; and a mineral composition having a reduced peculiar metal taste, of which administration is made easily.

4 Claims, 5 Drawing Sheets

OTHER PUBLICATIONS

Database WPI, Section Ch, week 199621 Derwent Publications Ltd., London, GB; AN 1996–205436 XP002182609, & JP 08 073350 A (Itoen KK), Mar. 19, 1996 *abstract*.

Database WPI, Section Ch, Week 199712 Derwent Publications Ltd., London GB; AN 1997–128646 XP002196610, & JP 09 012454 A (Taiyo Kagaku KK), Jan. 14, 1997 *abstract*.

* cited by examiner

COMPOSITION COMPRISING THEANINE

This application is a divisional application of Ser. No. 09/655,336, filed Sep. 5, 2000, which is a divisional application of Ser. No. 09/403,486, filed Oct. 22, 1999, which is a 371 of PCT/JP99/00784, filed Feb. 23, 1999, which claim foreign priority of JP applications 10-57470, filed Feb. 23, 1998, 10-142119, filed May 8, 1998, 10-234968, filed Aug. 6, 1998, 10-330207, filed Nov. 5, 1998.

TECHNICAL FIELD

The present invention relates to a theanine-containing composition which can be used for a food composition, a pharmaceutical composition, and the like, for suppressing and ameliorating various symptoms accompanying diminished homeostasis, such as obesity, anxiogenic symptoms, premenstrual syndrome, sensitivity to cold, menopausal disorders, sleep disorders and autonomic imbalance. Further, the present invention relates to a mineral composition in which a peculiar metal taste is reduced.

BACKGROUND ART

Conventionally, various symptoms accompanying diminished homeostasis, such as obesity, anxiogenic symptoms, premenstrual syndrome, sensitivity to cold, menopausal disorders, sleep disorders and autonomic imbalance, have been treated by symptomatic chemotherapies. A number of kinds of such symptoms, disorders, and the like can often develop concurrently with aging. In such case, great cautions should be exerted in prescribing drugs appropriate for individual symptoms, e.g., hormones, kampo medicines, tranquilizers, and the like, in combination, because unexpected adverse reactions can occur. There is therefore demand for a very safe composition, such as a food composition, for mitigating and ameliorating such complicating symptoms without the aid of drugs.

Although a wide variety of causes are involved in the pathogenesis of these diseases, it is a key to their prevention and treatment to improve our dietary life. In other words, imbalanced nutrient intake also contributes to the development of the aforementioned diseases, despite the recent enrichment of our dietary life. Nutrition surveys have demonstrated that the minimum requirements are not satisfied for some minerals. Against this background, minerals have recently been added to foods, beverages, supplements, nutrition enhancers, and the like; however, their peculiar metal tastes limit the amount of their addition or reduce their commercial value.

Therefore, an object of the present invention is to provide a composition for suppressing and ameliorating the above symptoms. Particularly, it is to provide a composition having high safety, the composition of which the method of administration is simple, even in the case of the complicated symptoms. Further, it is to provide a mineral composition, of which a peculiar metal taste is reduced and administration is made easy. These and other objects of the present invention will be apparent from the following description.

DISCLOSURE OF INVENTION

As a result of intensive studies in view of solving the above problems, the present inventors have found that theanine has marked effects in suppression and amelioration against various symptoms. In this case, not only the composition comprising theanine, but also the composition comprising a mineral as well as theanine would also allow to provide mineral supplement. The present inventors have found that this composition has a reduced peculiar metal flavor, so that they have found a mineral composition to easily allow mineral supplement. Based on these findings, the present inventors have completed the present invention.

Specifically, in essence, the present invention pertains to:

[1] a composition for suppressing or ameliorating a symptom accompanying diminished homeostasis, comprising theanine; and

[2] a mineral composition comprising theanine and a mineral.

BEST MODE FOR CARRYING OUT THE INVENTION

1. Theanine-Containing Composition

Figure 1:
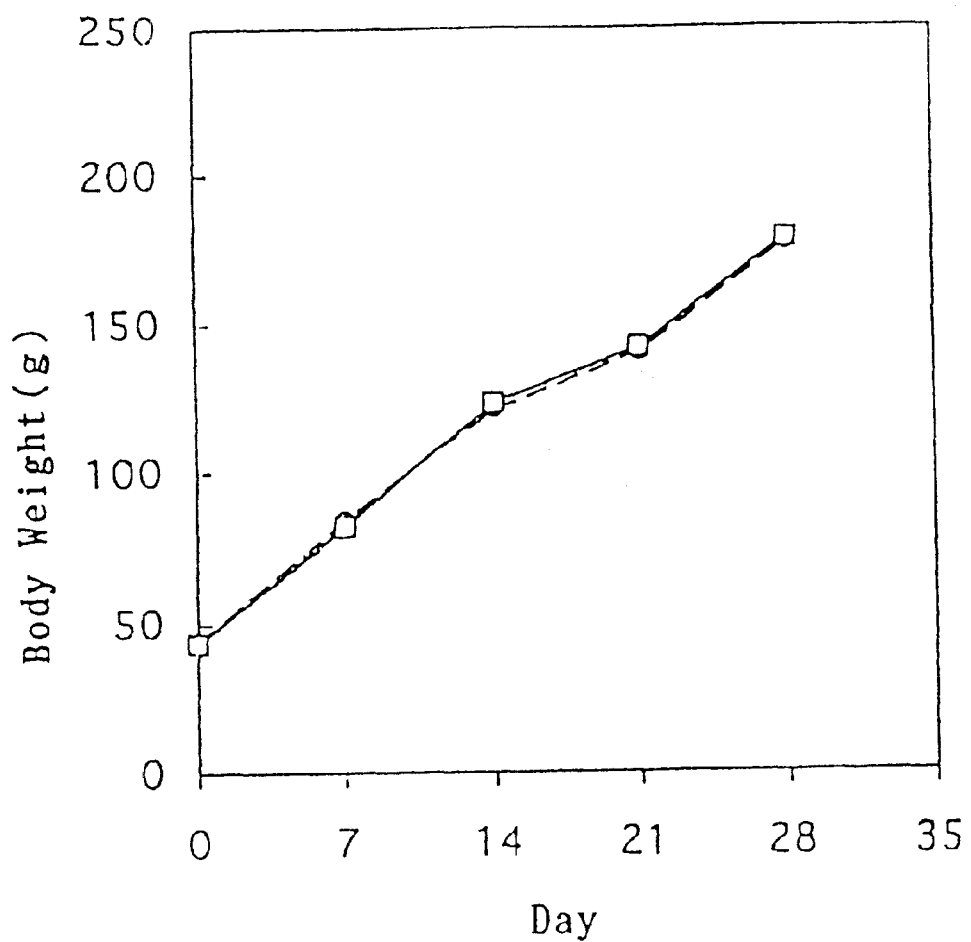
FIG. 1 is a graph showing the influence of theanine on the body weight increase of young female rats. In the figure, □ are data for the inventive products; and ● are control data, respectively.

Theanine, formulated in the theanine-containing composition of the present invention, is a glutamic acid derivative contained in tea-leaves, which is the main component of deliciousness (umami) of tea. It is also used as a food additive for seasoning. Regarding its safety, there are no dead cases of animals receiving an oral administration of 2 g/kg in acute toxicity test with mice, nor was there any abnormal finding in gross condition or body weight. As described above, the theanine is an extremely safe substance.

The method for detecting theanine in the composition of the present invention is not particularly limited, and preference is given to the method comprising derivatizing with ortho-phthalaldehyde (OPA) at a pre-column, thereafter separating by high performance chromatography with an ODS column, and detecting and quantifying theanine with a fluorescence detector.

Examples of methods for preparing theanine used in the present invention include an organic synthesis method [*Chem. Pharm. Bull.*, 19(7), 1301–1307 (1971)]; fermentation methods (Japanese Patent Laid-Open Nos. Hei 5-68578 and Hei 5-328986); or modification methods thereof using an ethylamine derivative, such as ethylamine hydrochloride, in place of ethylamine; a method comprising reacting pyroglutamic acid with ethylamine hydrochloride (Japanese Patent Laid-Open No. Hei 9-263573); a plant cell culture method (Japanese Patent Laid-Open No. Hei 5-123166); and a method using extraction from tea-leaves, with preference given to the fermentation methods, which permit the obtainment of theanine in large amounts at low costs. The term "tea-leaves" as used herein refers to green tea, oolong tea, black tea, and the like.

In addition, any of L-theanine, D-theanine and DL-theanine are usable, among which the L-form is preferred in the present invention, because it is approved as a food additive, and it is economically utilizable. In addition, the theanine used in the present invention may be of any forms, such as purified products, crudely purified products, extracts, and the like.

The composition of the present invention may further comprise a mineral. The composition comprising minerals is more preferable, because it can supplement essential elements and trace essential elements, which tend to be deficient in living bodies. The mineral content in the composition, for example, is preferably from 0.0001 to 99.9% by weight and more preferably 0.01 to 99.9% by weight. As described in detail in the section of "Mineral Composition" below, the term "minerals" as used herein refers to metals essential for the maintenance and regulation of living bodies, such as iron, magnesium, copper, zinc, selenium, calcium, potassium, manganese, chromium, iodine, molybdenum, nickel and vanadium, or salts thereof, wherein their content is calculated as the amount of these metal elements. The mineral may be constituted by of a single metal element or a plurality of metal elements.

In addition, the theanine can be used in combination with other ingredients. The other ingredients are not particularly limited, and examples thereof include herbs, such as Saint John's-wort and chamomile; kampo medicinal plants, such as *Gymnema sylvestre, Garcinia cambogia, Eucommia ulmoides* and ginseng, or extracts thereof; animal extracts, such as placenta extract; functional materials, such as dietary fiber and soybean peptide; vitamins; and dieting sweeteners, with preference given to functional materials, such as dietary fiber and soybean peptide.

The composition of the present invention comprising theanine has suppressive effect and ameliorating effect on various diseases. For the purpose of suppressing and ameliorating symptoms accompanying diminished homeostasis, concretely for obesity suppression, suppression of anxiogenic symptoms, suppression of premenstrual syndrome, amelioration of sensitivity to cold, amelioration of menopausal disorders, amelioration of sleep disorders and amelioration of autonomic imbalance, the composition of the present invention can be used.

The term "diminished homeostasis" as used in the present invention is defined as a state wherein the potential of an organism for stably maintaining its morphological and physiological conditions in normal ranges using the nervous, endocrine, circulatory and immune systems, while undergoing various external and internal changes, to ensure survival as an individual has been diminished. Specific symptoms include bad physical condition and mental anxiety due to hormone hypersecretion, deficiency, and the like, and autonomic imbalance symptoms, such as stiff shoulders, headache, vertigo, sensitivity to cold, irritation, palpitation, short breath, dyspnea, numbness and insomnia.

The amount of administration of the theanine for sufficiently exhibiting the suppressive effect for diminished homeostasis is preferably from 0.2 to 2,000 mg/kg·day, more preferably from 0.2 to 300 mg/kg·day. However, since there are individual differences in the kinds of symptoms and the degree of progression, the amount of administration of the theanine in the present invention is not limited to the ranges specified above.

The content of the theanine in the composition of the present invention may be appropriately adjusted depending upon the concrete symptoms, ages, number of administration, and the like. For example, the content of the theanine in the composition is preferably from 0.00025 to 100% by weight, more preferably 0.005 to 100% by weight.

The term "obesity" as used in the present invention refers to a form of obesity accompanied by complications due to over-accumulation of fat, which is caused by overeating, inappropriate eating style, lack of exercise, heredity, thermogenesis disorders or an unidentified cause.

As for suppressing an effect for obesity, a satisfactory effect can be obtained when the theanine is preferably administered at 0.3 mg/kg·day or more, and as the amount of the administration is increased, its effect is further enhanced. Since the theanine is a highly safe substance, the amount of administration is not particularly limited. It is desired that the amount of administration does not exceed the level of 2,000 mg/kg·day. Therefore, the amount of administration of the theanine for sufficiently exhibiting the suppressive effect for obesity is preferably from 0.3 to 2,000 mg/kg·day, more preferably from 0.3 to 100 mg/kg·day, still more preferably from 0.3 to 50 mg/kg·day.

The composition of the present invention can be used to suppress anxiogenic symptoms. The term "anxiogenic symptoms" as used in the present invention refers to a form of anxiogenic symptoms due to continuous or habitual intake of a methylxanthine derivative or an unidentified cause. Continuous or habitual intake of a methylxanthine derivative is said to promote anxiety symptoms, which can lead to panic disorders characterized by the sudden development of severe anxiety together with palpitation, vertigo and other symptoms; continuous or habitual intake of a methylxanthine derivative is said to be a cause of panic disorders. The methylxanthine derivative mentioned here is exemplified by caffeine, theophylline and theobromine. Forms of methylxanthine derivatives are not particularly limited, and they include natural or synthetic purified products, foods and pharmaceuticals supplemented therewith, coffee, cocoa, green tea, fermented teas, such as black tea, semi-fermented teas, such as oolong tea, or processed products therefrom.

As for suppressing anxiogenic symptoms, a satisfactory effect can be obtained when the theanine is preferably administered at 0.3 mg/kg·day or more, and as the amount of administration is increased, its effect is further enhanced. Although there is no upper limit for the amount of administration of the theanine, it is generally preferable that the amount of administration does not exceed about 300 mg/kg·day, when taken into consideration of the distinctive taste and economic advantages of the theanine. Therefore, the amount of administration of the theanine for sufficiently exhibiting the suppressive effect for anxiogenic symptoms is preferably from 0.3 to 300 mg/kg·day, more preferably from 0.3 to 30 mg/kg·day, and still more preferably from 0.3 to 3 mg/kg·day.

The term "premenstrual syndrome (PMS)" as used in the present invention is defined as a series of various symptoms that can interfere with daily life of the patient, due to a hormone imbalance, occurring in the high basal body temperature phase, i.e., the ovarian corpus lutea stage, starting about 2 weeks before menstruation in females.

More than 150 symptoms can be developed, including physical symptoms, such as sleepiness, fatigability, stiff breasts, painful breasts, likelihood to have acne, chapped skin, bad spread of cosmetics, increased vaginal discharge, inability to take smooth body action, allergic symptoms, headache, head stuffiness, stiff shoulders, vertigo, limb coldness, abdominal pain, lower abdominal pain, lower abdominal stiffness, lumbago, swelling, thirst, constipation, diarrhea, increased appetite, decreased appetite and food preference change; mental symptoms, such as depressive state, spiritlessness, irritation, aggressiveness, faintheartedness, maudlinness, solitariness, loneliness, anxiety, psychological lift, inability to concentrate, decreased work efficiency, increased sexual desire and decreased sexual desire; and social symptoms, such as autism, mysophobia, inability to manage one's health, repugnance to menstruation, weariness of doing anything, inability to work as usual, repugnance to being female, quarrels with others, staying at home, craving to be alone, craving to waste money, railing at one's families and friends, and unsociableness, without being limited thereto.

The amount of administration of the theanine for sufficiently exhibiting the suppressive effect for premenstrual syndrome is preferably from 0.2 to 200 mg/kg·day, more preferably from 0.5 to 50 mg/kg·day.

The term "sensitivity to cold" as used in the present invention refers to a subjective symptom of pain of cold in the body and each sites of the body, which is a relatively chronic recognition of cold, not caused by drastic external causes.

The amount of administration of the theanine for sufficiently exhibiting the amelioration effect for sensitivity to cold is preferably from 0.2 to 200 mg/kg·day, more preferably from 0.5 to 50 mg/kg·day.

The term "menopausal disorders" as used herein is defined as a series of health condition changes occurring when gonadotropin is hypersecreted as the amount of progesterone and estrogen secreted decreases. Specific symptoms include autonomic abnormalities, such as hot sensation, flushing, palpitation, excess sweating and sensitivity to cold; mental symptoms, such as depression, fretfulness, anxiety, insomnia, tinnitus, numbness, diarrhea, pollakiuria, hypomnesia and diminished judgment; and other symptoms, such as stiff shoulders, lumbago and malaise.

The amount of administration of the theanine for sufficiently exhibiting the amelioration effect for menopausal disorders is preferably from 0.2 to 200 mg/kg·day, more preferably from 0.5 to 50 mg/kg·day.

The amount of administration of the theanine for sufficiently exhibiting the amelioration effect for sleep disorders is preferably from 0.2 to 200 mg/kg·day, more preferably from 0.5 to 50 mg/kg·day.

Regarding the embodiment of use of the composition of the present invention, it can advantageously be used for a food composition or a pharmaceutical composition. The term "food composition" as used in the present invention encompasses theanine-containing food additives, as well as theanine-containing foods. When used for a food composition, the composition of the present invention may be prepared by, for example, formulating the theanine in any one of the foods shown below.

Specifically, the theanine can be formulated in dry foods, supplements, and liquid foods, such as soft drinks, mineral water, luxury beverages and alcoholic beverages. Beverages which may be mentioned herein are not particularly limited, and examples thereof include teas, such as green tea, oolong tea, black tea and herb tea, fruit juice concentrates, reconstituted juice concentrates, fresh juices, mixed fruit juices, fruit grain-containing fruit juice, fruit juice-containing beverages, mixed fruit/vegetable juice, vegetable juice, carbonated beverages, soft drinks, milk beverages, Japanese sake, beer, wine, cocktails, shochu and whiskey. In addition, crude drugs, herbs, amino acids, vitamins and other materials and ingredients which are acceptable for foods may be used together in combination with the theanine. Crude drugs used herein are not particularly limited, and examples thereof include Japanese valerian, Japanese angelica root, peony root, moutan, ginseng, and the like, which are effective in keeping a good hormone balance in females. Herbs are not particularly limited, and examples thereof include anise, carrot seed, clove, coriander, cypress, cinnamon, juniper, ginger, sweet orange, pine needle, basil, patchouli, bitter orange, fennel, black pepper, bay, peppermint, bergamot, mandarin, myrrh, lemongrass, rosemary, grapefruit, cedarwood, citronella, sage, thyme, tea tree, violet leaf, vanilla, hyssop, eucalyptus, lime, lemon, ylang-ylang, cardamon, clary sage, jasmine, geranium, chamomile, Bulgarian rose, rose, olibanum, lavender, chamomile, geranium, sandalwood, neroli, verbena, petigrain, vetiver, marjoram, lemon balm (*Melissa officinalis*), rosewood, Saint John's-wort, Saint John's-wort and kawakawa, with preference given to peppermint, bergamot, ylang-ylang, geranium, chamomile, lavender, Saint John's-wort and kawakawa, all of which have sedative and relaxing effects. The forms of these herbs are not particularly limited, and examples thereof include extract, essential oil and herb tea. The amino acids used are not limited, and examples thereof include glutamine, glutamic acid, inosinic acid, alanine, arginine, aspartic acid, threonine, serine, γ-aminobutyric acid, taurine, thiotaurine and hypotaurine. The vitamins used are not particularly limited, and examples thereof include vitamin A, vitamin $B_1$, vitamin $B_2$, vitamin $B_6$, vitamin $B_{12}$, vitamin C, vitamin D, vitamin E, vitamin K, folic acid, nicotinic acid, lipoic acid, pantothenic acid, biotin and ubiquinone, as well as derivatives thereof. In addition, other useful substances include aloe, royal jelly, melatonin, placenta, propolis, isoflavone, soybean lecithin, egg yolk lecithin, egg yolk oil, chondroitin, cacao mass, collagen, vinegar, chlorella, spirulina, gingko leaf, green tea, tochu tea, Chinese wolfberry tea, oolong tea, mulberry leaf, *Rubus suavissimus,* banaba tea, unsaturated fatty acids, saccharides such as oligosaccharides, bifidobacteria, fungi such as red koji, mushrooms such as *Agaricus blazei, Agaricus blazei,* ganoderma and *Grifola frondosa,* fruits such as blueberry, prune, grape, olive, ume and citruses, seeds such as peanuts, almonds, sesame and pepper, vegetables such as green pepper, chili, Welsh onion, pumpkin, melon, carrot, great burdock, jute leaf (*Corchorus capsularis*), garlic, perilla, wasabi, tomato, scallion, leaf vegetables, tubers and pulses, seaweeds such as wakame, fishes, animal meat/poultry/whale meat and cereals, as well as extracts, dry products, crudely purified products, purified products, processed products, fermented products and other products therefrom.

When the theanine-containing composition of the present invention is used for a pharmaceutical composition, its form is not particularly limited, and it may be prepared as any one of solutions, suspensions, powders, molded solids, and the like. Therefore, the theanine-containing composition of the present invention can be provided as capsules, tablets, powders, granules, drinks, and the like. In addition, the theanine-containing composition of the present invention can be used in combination with other pharmaceuticals. The pharmaceutical composition is expected to have the same effects as those of the aforementioned food composition.

The method for preparing the composition of the present invention is not particularly limited, and general preparation methods for foods and pharmaceuticals may be used, including a method comprising mixing theanine and other ingredients in a powder; a method comprising dissolving theanine and other ingredients in a solvent to yield a mixed solution; a method comprising freeze-drying the resulting mixed solution; and a method comprising spray-drying the mixed solution. For example, the composition can be obtained by formulating theanine and other ingredients with commonly known excipients, carriers, binders, stabilizers, and the like.

2. Mineral Composition

The mineral composition of the present invention comprises theanine and a mineral. The mineral used in the present invention, which is the same as that described in the above section of Theanine-Containing Composition, is an essential metal for maintenance and regulation of living bodies, such as iron, magnesium, copper, zinc, selenium, calcium, potassium, manganese, chromium, iodine, molybdenum, nickel and vanadium. Its form includes salts, oxides, protein complexes, or complexes of degraded products thereof; polysaccharides or complexes of degraded products thereof; other processed starch complexes; cyclodextrin complexes; metal enzymes comprising minerals, such as superoxide dismutase, glutathione peroxidase and acidic phosphatase; metal-activated enzymes such as phosphoglucomutase; enzymes and coenzymes containing a metal at sites other than the active center sites, and the like. These minerals may be those which are naturally occurring, and preferably those which are isolated and purified by a known method to increase its mineral content. Here, one embodiment of the form of the mineral will be shown.

The iron compound includes iron, ferrous sulfate (dry), ferrous sulfate (crystalline), iron citrate, ferrous gluconate, ferrous pyrophosphate, ferric pyrophosphate, ferrous pyrophosphate solution, ferric pyrophosphate solution, ferric chloride, iron lactate, iron ammonium citrate, diiron trioxide, ferritin, transferrin, ovotransferrin, heme iron, and the like. The magnesium compound includes magnesium carbonate, magnesium sulfate, magnesium chloride, magnesium oxide, magnesium L-glutamate, and the like. The copper compound includes copper sulfate, copper gluconate, and the like. The zinc compound includes zinc sulfate, zinc gluconate, zinc dioxide, and the like. The selenium compound includes selenocysteine, selenomethione, and the like. The calcium compound includes calcium chloride, calcium carbonate, calcium hydroxide, calcium lactate, calcium gluconate, calcium citrate, calcium L-glutaminate, calcium pantothenate, calcium glycerophosphate, calcium 5'-ribonucleotide, calcium sulfate, tricalcium phosphate, calcium monohydrogenphosphate, calcium propionate, calcium dihydrogenphosphate, calcium dihydrogenpyrophosphate, calcium salt of carboxymethyl cellulose, calcium stearoyl lactate, calcium disodium ethylenediaminetetraacetate, calcined calcium of sea urchin shells, calcined calcium of sea shells, calcined calcium of bones, calcined calcium of coral, calcined calcium of milk sera, calcined calcium of eggshells, non-calcined calcium of sea shells, non-calcined calcium of bones, non-calcined calcium of coral, non-calcined calcium of pearl layer, non-calcined calcium of egg shells, high-degree bleaching powder, and the like.

The mineral composition of the inventive product may be used as it is, or it may be used as dry foods, supplements, and liquid foods, such as soft drinks, mineral water, luxury beverages and alcoholic beverages, and the like. In addition, as for the pharmaceuticals, the mineral composition is added to tablets, powders, granules, drinks, and the like, and the mixture is formed into preparation for use. In addition, the mineral composition may be used in combination with essential oils, amino acids, vitamins and other ingredients. Particularly, the combined use of the mineral composition and vitamins is effective in improvement of metal taste of the fruits and the processed products thereof. The content of the mineral in the mineral composition is not particularly limited, and the content thereof in the composition, calculated as a metal element, is preferably from 0.0001 to 99.9% by weight, more preferably from 0.01 to 99.9% by weight.

The theanine contained in the mineral composition may be any of L-form, D-form, and DL-form. Among them, the L-form is preferable because its improvement of the effect of the metal taste is high.

Since the theanine is highly safe, its content in the composition is not particularly limited. The content of the theanine differs depending upon the strength of the metal taste. Concretely, in order that the mineral composition sufficiently exhibits its effects, the content of the theanine preferably ranges from $10^{-3}$ to $10^6$, more preferably from $10^{-1}$ to $10^5$, still more preferably from $10^{-1}$ to $10^4$, per 1 of the metal content in the mineral composition in a weight ratio. From the viewpoint of exhibiting the effects resulting from the formulation of the theanine, the content is preferably $10^{-3}$ or more, and in consideration of the amount of the mineral to be contained in the mineral composition, the content is $10^6$ or less.

Since the theanine is formulated in the mineral composition, astringent taste, bitter taste, sour taste, salty taste, pungent taste, puckery taste, hot taste, and the like owned by the conventional mineral composition are modified.

The method for preparing the mineral composition of the present invention is not particularly limited, and examples thereof include a method comprising mixing minerals with theanine in a powder; a method comprising dissolving minerals and theanine in a solvent, such as water, to yield a mixed solution; a method comprising freeze-drying the resulting mixed solution; a method comprising spray-drying the mixed solution, and the like.

The present invention will be described in further detail by means of the following working examples and test examples, but the present invention is by no means limited to these working examples.

EXAMPLE 1

Glutaminase in an amount of 0.3 U per 1 ml of the buffer was added to boric acid buffer (disodium borate-sodium hydroxide, pH 11) containing 0.3 M glutamine and 1.5 M ethylamine, and the mixture was incubated at 30° C. for 22 hours to react the components. Two-hundred and twenty-five millimoles of theanine was isolated from 1 L of the reaction mixture. Incidentally, a by-product, glutamic acid, was 20 mmol. Theanine was isolated and purified from the reaction mixture by applying the reaction mixture to a Dowex 50×8, Dowex 1×2 column chromatography and eluting with ethanol.

The isolated substance was applied to amino acid analyzer-paper chromatography. From the fact that the isolated substance exhibited the same behavior as standard substance of theanine, there was confirmed that the isolated substance is theanine. When the isolated substance was hydrolyzed with hydrochloric acid or glutaminase, glutamic acid and ethylamine were formed at a molar ratio of 1:1. Since the isolated substance was hydrolyzed with glutaminase, it was shown that ethylamine was bound to glutamic acid at the γ-position. In addition, from the results of the reaction of glutamic acid formed by hydrolysis with glutamic acid dehydrogenase (GLuDH), there was confirmed that glutamic acid is L-form. From this finding, there was confirmed that the isolated substance is L-theanine.

EXAMPLE 2

Ten kilograms of tea leaves (*Camellia sinensis L.*) were extracted with boiling water. The resulting extract was applied to a cation exchange resin ("Dowex HCR W-2," manufactured by Muromachi Kagaku Kogyo K.K.), and eluted with 1 N NaOH. The eluted fraction was applied to an activated carbon ("Taiko Kasseitan SG" manufactured by Futamura Kagaku Kogyo K.K.), and eluted with 15% EtOH, to give an eluted fraction. The resulting eluted fraction was concentrated using an RO membrane (Nitto Denko "NTR 729 HF"), and then purified by column chromatography, to give a purified product. Furthermore, the purified product was recrystallized, to give 24.8 g of L-theanine.

Test Example 1

In order to confirm the safety of L-theanine obtained in Examples 1 and 2, each of 3 week-old young female rats (7 rats/group) was orally administered with 1 ml of a 20% aqueous solution of theanine (inventive product), per 100 g of body weight with a probe, once a day, for 28 days. The rats of the control group were administered with 1 ml of water, per 100 g of body weight with a probe. The body weights of the rats were measured before administration, and 7, 14, 21 and 28 days after the administration. The results are shown in FIG. 1. As shown in FIG. 1, the growth suppression could not be observed, and dead cases were not confirmed by the administration of the inventive product.

Test Example 2

Figure 2:
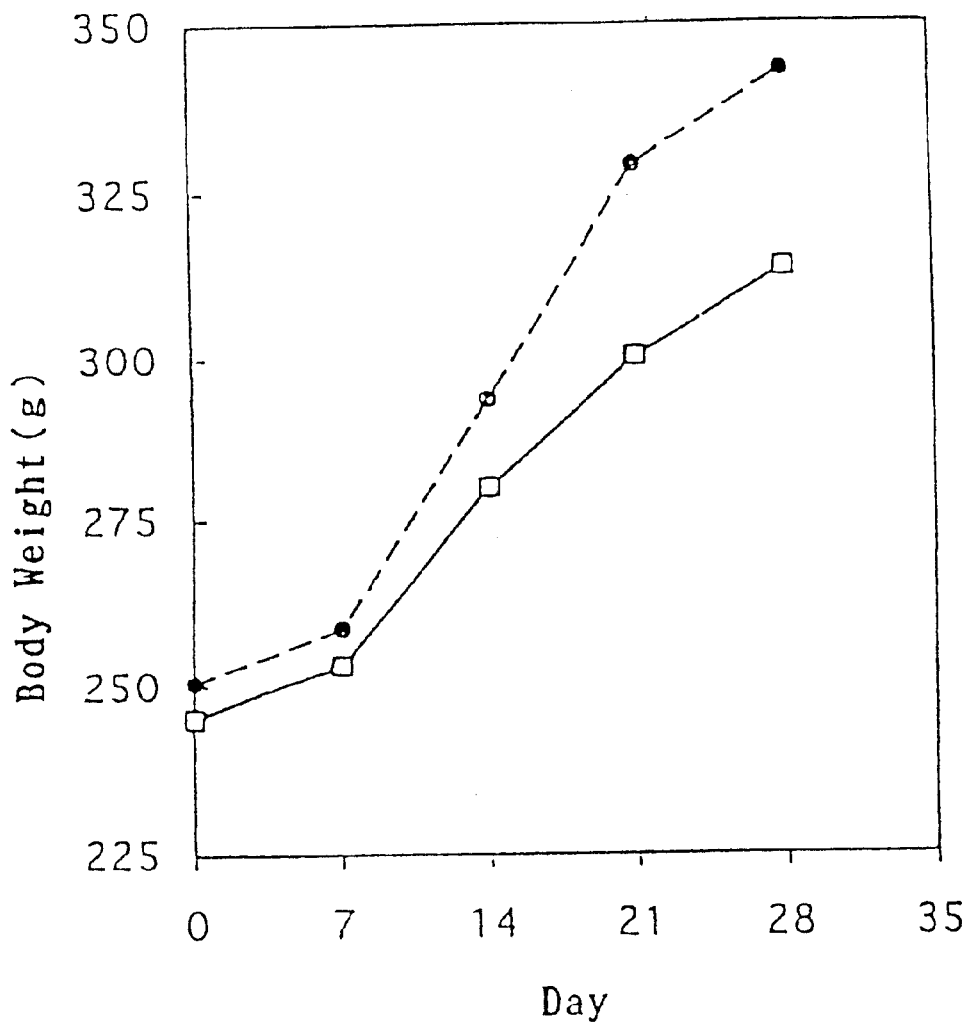
FIG. 2 is a graph showing the effect for obesity suppression of theanine in the ovariectomized rats. In the figure, □ are data for the inventive products; and ● are control data, respectively.

The effect of the obesity suppression of the inventive product on rats was tested. Each of L-theanine obtained in Example 1 and Example 2 was dissolved in 1 ml water (inventive product) at 20 mg per 1 body weight of 10 week-old ovariectomized rats (7 rats/group). Each of the rats was orally administered with a probe once a day for 28 days. The rats were fed freely with high sucrose diet, and given free access to drinking water. The rats of the control group were administered with 1 ml of water with a probe. The body weights of the rats were measured before administration, and 7, 14, 21 and 28 days after the administration. After the end of the administration periods, the rats were dissected, and the weights of their visceral fats and sera cholesterol levels were measured. The results of the weight are shown in FIG. 2. As shown in FIG. 2, the body weight increase in menopausal disorders was remarkably suppressed by the administration of the inventive product. In addition, the results of the weight of visceral fats and the sera cholesterol level are shown in Table 1.

TABLE 1

|  | Amount of Visceral Fats (g) | Sera Cholesterol Level (mg/dl) |
|---|---|---|
| Control | 18.73 ± 1.37 | 93.18 ± 14.7 |
| Administration of Inventive Product | 7.50 ± 0.6 | 60.06 ± 21.57 |

EXAMPLE 3

Iron lactate and L-theanine obtained in Example 1 were mixed in a mixing ratio of 4:1, to give a granular inventive product.

EXAMPLE 4

Zinc sulfate and L-theanine obtained in Example 2 were mixed in a mixing ratio of 1:40. To 3 parts of the resulting composition was added 17 parts of water, to prepare a mixed aqueous solution. The mixed aqueous solution was spray-dried, to give a granular inventive product.

EXAMPLE 5

Magnesium sulfate and L-theanine obtained in Example 1 were mixed in a mixing ratio of 1:1000. To 5 parts of the resulting composition was added 15 parts of water, to prepare a mixed aqueous solution. The mixed aqueous solution was spray-dried, to give a granular inventive product.

Test Example 3

The inventive product was tested on the suppressive effect of the anxiogenic symptoms in humans. The test was performed on six subjects selected from among individuals who were accustomed to take about 6 cups or more of coffee daily, and were categorized in the high-anxiety group by the MAS method for evaluating the degree of manifested anxiety [Taylor, Abe, Takaishi; "Manifest Anxiety Scale (MAS) Instruction Manual", Sankyo Shobo, 1968]. In the test, an aqueous solution of the composition having the suppressive effect of the anxiogenic symptoms was prepared by dissolving 50 mg of L-theanine as obtained in Example 1 in 100 g of mineral water (hereinafter referred to as "anxiogenic symptoms-suppressive composition water") (equivalent to about 0.8 mg/kg). Each subject was requested to drink the anxiogenic symptoms-suppressive composition water three times daily, and after 2 weeks, the degree of anxiety was again evaluated by the MAS method. As a result of drinking the anxiogenic symptoms-suppressive composition water for 2 weeks, 5 out of the 6 subjects were categorized in the low-anxiety group and 1 subject categorized in the moderate-anxiety group, demonstrating amelioration in the symptoms.

Test Example 4

Each of male and female subjects consisting of a total of 7 members was given a beverage prepared by dissolving the L-theanine obtained in Examples 1 and 2 at amounts of 0 mg, 60 mg, 300 mg or 1200 mg in 100 g of coffee extract in boiling water (equivalent to about 1 mg/kg, about 5 mg/kg, and about 200 mg/kg, respectively) 10 times per day for one month. The results thereof are shown in Table 2.

TABLE 2

| Theanine Content | 0 mg | 60 mg | 300 mg | 1200 mg |
|---|---|---|---|---|
| High-Anxiety Group | 4 | 2 | 0 | 0 |
| Moderate-Anxiety Group | 3 | 3 | 1 | 0 |
| Low-Anxiety Group | 0 | 2 | 0 | 7 |

As shown in Table 2, the number of subjects complaining to be in the high-anxiety group and the moderate-anxiety group decreased in accordance with the increase in the amount of administration of theanine.

EXAMPLE 6

Theanine-containing candies were prepared with the composition shown in Table 3 by using the L-theanine prepared in Example 1. Incidentally, the content of the L-theanine in candies was measured, and as a result, the content was found to be 89.6 mg/g.

TABLE 3

Theanine-Containing Candies

| | |
|---|---|
| 1. Granulated Sugar | 64 parts |
| 2. Malt Syrup | 23 parts |
| 3. L-Theanine | 10 parts |
| 4. Flavor (Lemon Flavor) | 0.05 parts |
| 5. 50% Tartaric acid | 1 part |
| 6. Water | 30 parts |

Ingredient 1 was dissolved completely in 20 parts of water, with heating to 110° C. Ingredient 3 was dissolved in the remaining water, and the mixture and Ingredient 2 were added. The temperature of the mixture was raised to 145° C. After the stove was turned off, Ingredient 5 was added thereto, and mixed. The mixture was cooled to 75° to 80° C., formed with a forming roller, to prepare theanine-containing candies.

EXAMPLE 7

A theanine-containing blueberry beverage was prepared with the composition shown in Table 4 by using the L-theanine prepared in Example 2. Incidentally, the L-theanine in the blueberry beverage was quantified, and as a result, the content was found to be 98.3 mg/100 ml.

TABLE 4

Theanine-Containing Blueberry Beverage

| | |
|---|---|
| 1. Isomerized Sugar | 12 parts |
| 2. Blueberry Concentrated Fruits Juice | 1.0 part |
| 3. ⅕ Transparent Lemon Juice | 0.4 parts |
| 4. Sodium Citrate | 0.05 parts |
| 5. 50% Sodium Citrate (Crystalline) | for pH adjustment |
| 6. L-Theanine | 0.1 parts |
| 7. Flavor (Blueberry Flavor) | 0.07 parts |
| 8. Water | Balance |

Ingredients 1 to 4, 6 and 8 were dissolved by stirring. The pH of resulting mixture was adjusted to 3.1 with Ingredient 5, and thereafter the mixture was heated to 95° C. After adding Ingredient 7 to the mixture, the resulting mixture was filled and cooled, to prepare a theanine-containing blueberry beverage.

A theanine-containing grapefruits beverage was prepared with the composition shown in Table 5 by using the L-theanine prepared in Example 2. Incidentally, the L-theanine in the grapefruits was quantified, and as a result, the content was found to be 96.4 mg/100 ml.

TABLE 5

Theanine-Containing Grapefruits Beverage

| | |
|---|---|
| 1. Isomerized Liquid Sugar | 6 parts |
| 2. L-Theanine | 0.1 parts |
| 4. Ferric Pyrophosphate | 0.06 parts |
| 5. Placenta Extract | 0.01 parts |
| 6. 100% Grapefruits Juice | 30 parts |
| 7. Sodium Citrate | for pH adjustment |
| 8. Flavor (Grapefruits Flavor) | 0.05 parts |
| 9. Water | Balance |

Ingredients 1 to 6, and 9 were dissolved by stirring. The pH of resulting mixture was adjusted to 3.1 with Ingredient 7, and thereafter the mixture was heated to 95° C. After adding Ingredient 8 to the mixture, each of 50 ml of the mixture was filled and cooled, to prepare a theanine-containing grape fruits beverage.

Test Example 5

A test for assessing the premenstrual syndrome-suppressive effect of the inventive product was performed in 20 women complaining of 5 or more premenstrual syndrome symptoms. The inventive product used herein was powdered L-theanine as prepared in Example 1. Each subject was requested to measure her basal body temperature upon awaking for 2 months. During the second month, 50 mg of powdered L-theanine per day was taken whenever a PMS-suggesting symptom developed during the corpus lutea stage from the day of suspected ovulation to the first day of menstruation in reference to the data compiled during the first month. During the test period, physical symptoms, mental symptoms and social symptoms were recorded in detail everyday. On the first day of the third menstruation, the test was terminated and a questionnaire survey was conducted. The questionnaire and results thereof are shown below.

Questionnaire Survey Concerning Premenstrual Syndrome of Test Example 5

1. Were PMS symptoms suppressed ?

1) having remarkable effects;

2) having some effects;

3) having slight effects;

4) none.

2. For those selected 1), 2) or 3) in 1., were there any improvements in the daily life ?

1) improved to almost the same level as normal;

2) improved;

3) slightly improved;

4) none.

3. For those selected 1), 2) or 3) in 1., please give specifics:

Physical symptoms:

Mental symptoms:

Social symptoms:

Questionnaire Results of Test Example 5

1. Were PMS symptoms suppressed ?

| | |
|---|---|
| 1) having remarkable effects | 6 subjects (30%); |
| 2) having some effects | 8 subjects (40%); |
| 3) having slight effects | 6 subjects (30%); |
| 4) none | 0 subjects (0%). |

2. For those selected 1), 2) or 3) in 1., were there any improvements in the daily life ?

| | |
|---|---|
| 1) improved to almost the same level as normal | 4 subjects (20%); |
| 2) improved | 7 subjects (35%); |
| 3) slightly improved | 8 subjects (40%); |
| 4) none | 1 subject (5%). |

3. For those selected 1), 2) or 3) in 1., please give specifics:
Physical symptoms:
smooth body action, stiff shoulders healed, light-headedness, sleepiness disappeared, awaking in good humor, slept well, legs do not swell, not become drowsy, breast discomfort modified, bowel movement improved, allergy mitigated, appetite being the same as usual.
Mental symptoms:
able to relax, became cheerful, able to take positive attitude, became less irritable, became less worrisome.
Social symptoms:
able to concentrate on job, finding the job less burdensome, came to feel at ease.

Test Example 6

The inventive product was tested on the suppressive effect of the premenstrual syndrome in 20 women complaining of 3 or more symptoms of premenstrual syndrome. The test was carried out for about 2 months, and the first day of menstruation was defined as day 1. The first month was a control period. During the second month, the test was carried out for each of 10 subjects being given 2 pieces of the theanine-containing candies prepared in Example 6 or 2 pieces of placebo from the last day of the second menstruation. Each candy was taken at a certain time everyday. During the test period, physical symptoms, mental symptoms and social symptoms were recorded in detail everyday. On the first day of the third menstruation, the test was terminated and a questionnaire survey was conducted. The questionnaire and results thereof are shown below.
Questionnaire Survey Concerning Premenstrual Syndrome of Test Example 6
1. Were PMS symptoms suppressed by the intake of candy?
1) having remarkable effects;
2) having some effects;
3) having slight effects;
4) none.
2. For those selected 1), 2) or 3) in 1., were there any improvements in the daily life ?
1) improved to almost the same level as normal;
2) improved;
3) slightly improved;
4) none.
Questionnaire Results of Test Example 6
1. Were PMS symptoms suppressed by the intake of the candy ?

|  | 1) having remarkable effects | 2) having some effects | 3) having slight effects | 4) None |
| --- | --- | --- | --- | --- |
| Theanine Candy | 3 | 3 | 4 | 0 |
| Placebo | 0 | 0 | 3 | 7 |

2. For those selected 1), 2) or 3) in 1., were there any improvements in the daily life ?

|  | 1) equivalent to normal level | 2) improved | 3) slightly improved | 4) None |
| --- | --- | --- | --- | --- |
| Theanine Candy | 4 | 3 | 3 | 0 |
| Placebo | 0 | 0 | 2 | 8 |

Test Example 7

The inventive product was tested on the suppressive effect of the premenstrual syndrome in 20 women complaining of 5 or more symptoms of premenstrual syndrome. The test was carried out for about 2 months, and the first day of menstruation was defined as day 1. The first month was a control period. During the second month, the test was carried out for each of 10 subjects being given 200 ml of the theanine-containing blueberry beverage prepared in Example 7 or 200 ml of placebo from the last day of the second menstruation. Each beverage was taken at a certain time everyday. During the test period, physical symptoms, mental symptoms and social symptoms were recorded in detail everyday. On the first day of the third menstruation, the test was terminated and a questionnaire survey was conducted. The questionnaire and results thereof are shown below.
Questionnaire Survey Concerning Premenstrual Syndrome of Test Example 7
1. Were PMS symptoms suppressed by the intake of blueberry beverage ?
1) having remarkable effects;
2) having some effects;
3) having slight effects;
4) none.
2. For those selected 1), 2) or 3) in 1., were there any improvements in the daily life ?
1) improved to almost the same level as normal;
2) improved;
3) slightly improved;
4) none.
Questionnaire Results of Test Example 7
1. Were PMS symptoms suppressed by the intake of the beverage ?

|  | 1) having remarkable effects | 2) having some effects | 3) having slight effects | 4) None |
| --- | --- | --- | --- | --- |
| Theanine Beverage | 4 | 4 | 2 | 0 |
| Placebo | 0 | 0 | 2 | 8 |

2. For those selected 1), 2) or 3) in 1., were there any improvements in the daily life ?

|  | 1) equivalent to normal level | 2) improved | 3) slightly improved | 4) None |
| --- | --- | --- | --- | --- |
| Theanine Beverage | 5 | 2 | 3 | 0 |
| Placebo | 0 | 0 | 1 | 9 |

As shown in the results of Test Examples 5, 6 and 7, there could be confirmed that theanine has an extremely high effect for suppressing PMS symptoms.

Test Example 8

Male and female panelists consisting of a total of 10 members were subjected to a sensory test with a 0.1% aqueous solution of a mineral composition using the inventive product obtained in Example 3 or with a 0.08% aqueous solution of iron lactate. Their metal taste was ranked into five levels as 5: strong; 4: somewhat strong; 3: some metal taste; 2: slightly metal taste; and 1: no metal taste. The results are shown in Table 6.

TABLE 6

|  | 0.1% Aqueous Solution of Mineral Composition | 0.08% Aqueous Solution of Iron Lactate |
|---|---|---|
| Rank of Metal Taste | 1.2 | 3.9 |

As shown in the results of Table 6, in the case of the supplemented mineral composition, favorable results can be obtained.

Test Example 9

Male and female panelists consisting of a total of 10 members were subjected to a sensory test with a 0.04% mineral composition-supplemented yogurt using the inventive product obtained in Example 4 or with a 0.001% zinc sulfate-supplemented yogurt. Their metal taste was ranked into five levels as 5: strong; 4: somewhat strong; 3: some metal taste; 2: slightly metal taste; and 1: no metal taste. The results are shown in Table 7.

TABLE 7

|  | 0.04% Mineral Composition-Supplemented Yogurt | 0.001% Zinc Sulfate-Supplemented Yogurt |
|---|---|---|
| Rank of Metal Taste | 1.3 | 4.5 |

As shown in the results of Table 7, in the case of the supplemented mineral composition, favorable results can be obtained.

Test Example 10

Male and female panelists consisting of a total of 10 members were subjected to a sensory test with a 0.2% mineral composition-supplemented milk using the inventive product obtained in Example 5 or a 0.0002% magnesium sulfate-supplemented milk. Their metal taste was ranked into five levels as 5: strong; 4: somewhat strong; 3: some metal taste; 2: slightly metal taste; and 1: no metal taste. The results are shown in Table 8.

TABLE 8

|  | 0.2% Mineral Composition-Supplemented Milk | 0.001% Magnesium Sulfate-Supplemented Milk |
|---|---|---|
| Rank of Metal Taste | 1.2 | 4.7 |

As shown in the results of Table 8, in the case of the supplemented mineral composition, favorable results can be obtained.

EXAMPLE 8

The following raw materials were mixed and tableted, to prepare a theanine-containing mineral supplement:
theanine (trade name: "SUNTHEANINE" manufactured by Taiyo Kagaku Co., Ltd.) 0.5% by weight, zinc acetate 3.0% by weight, crystalline cellulose 6.0% by weight, reductive maltose 20.0% by weight, lactose 65.0% by weight, Aspartame 1.0% by weight, sucrose fatty acid ester 4.0% by weight, and silicon dioxide 0.5% by weight.

EXAMPLE 9

Twenty panelists were subjected to a sensory test for the theanine-containing mineral supplement prepared in Example 8 and the theanine non-containing supplement. The taste was ranked into five levels with respect to four items, wherein 5 was the best, the rank being expressed as an average value of 20 members. The results are shown in Table 9. As a result, there is obtained an effect of reduction of bitter taste of the mineral in the theanine-containing mineral supplement.

TABLE 9

|  | Theanine-Containing Composition | Theanine Non-Containing Composition |
|---|---|---|
| Bitter Taste | 3.8 | 2.8 |
| Astringent Taste | 4.1 | 1.9 |
| Metal Taste | 4.5 | 2.0 |
| Overall Rank | 4.3 | 2.2 |

EXAMPLE 10

Figure 3:
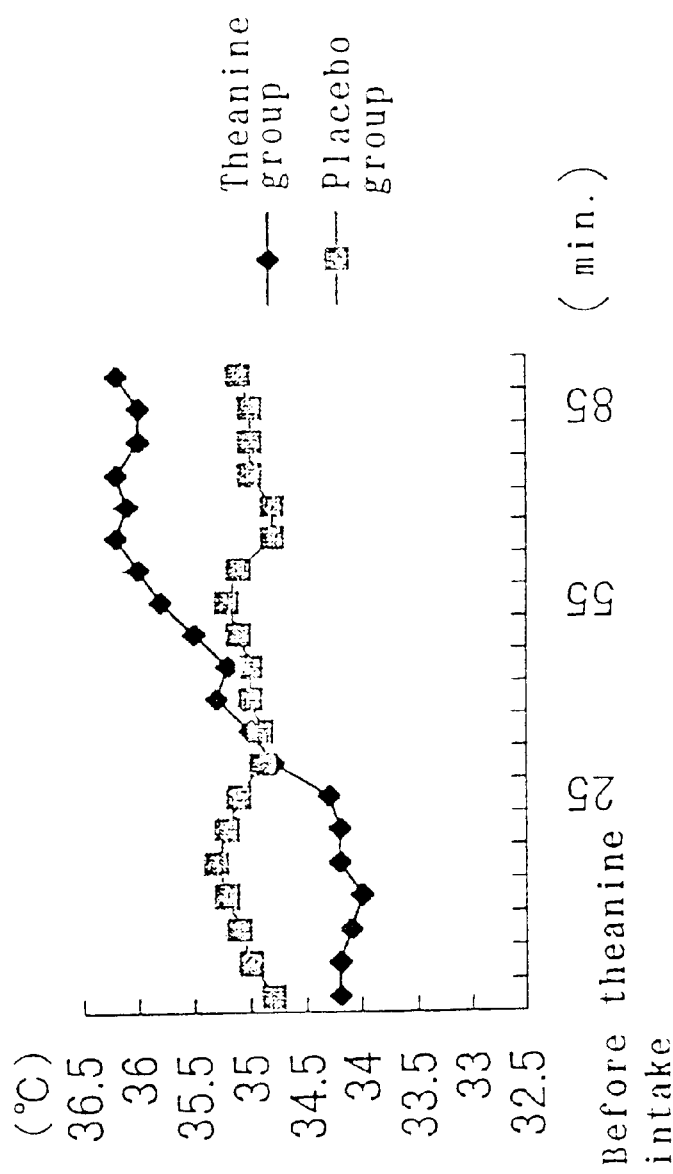
FIG. 3 is a graph showing the body temperature elevation effect by theanine. The abscissa of the graph shows the passage of period of time (minutes) after administration of a theanine-containing capsule or placebo, and the ordinate is the temperature of tip finger.

Ten women subjects complaining about their sensitivity to cold were requested to take two tablets of a theanine-containing capsule (200 mg/capsule) when they felt cold. The temperature of the tip finger was measured afterwards, and questionnaire survey was conducted. The same test was conducted to the placebo group, and a comparison was made therebetween. The results of the questionnaire survey are shown in Table 10, and the temperature variation of the tip finger is shown in FIG. 3.

TABLE 10

|  | Inventive Product Group | Placebo Group |
|---|---|---|
| Insensitive to cold in hands or feet | 9 | 1 |
| Body felt warm | 5 | 0 |

EXAMPLE 11

Figure 4:
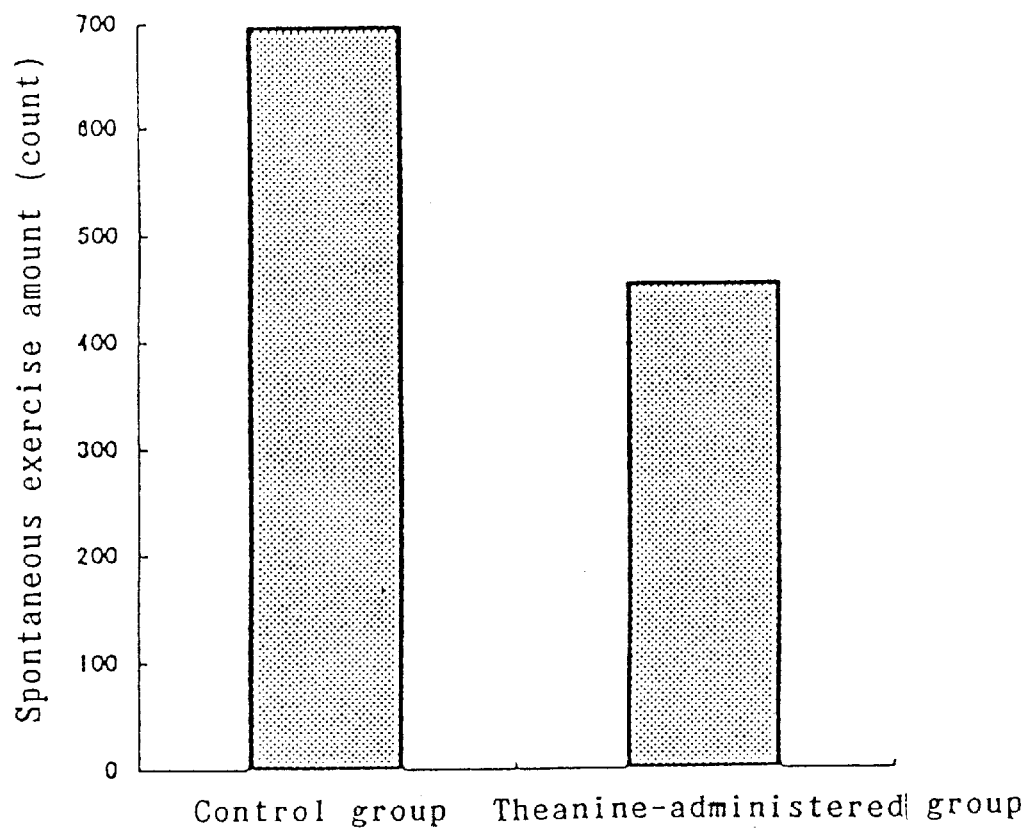
FIG. 4 is a graph showing the amount of spontaneous exercise for theanine-administered group and non-administrated group (control group), respectively.

Ten ICR male mice were each orally administered with 10 ml of a 1% by weight theanine aqueous solution, per 1 kg of body weight, and the mice were allowed to stand in an inhalation box. The administered group of mice were compared with the 10 non-administered group of mice, wherein the amount of excercise was evaluated by counting the number of rotations of the rotatable cage for 60 minutes. The results are shown in FIG. 4. As shown in the figure, a significant decrease in the amount of exercise was found by the administration of theanine.

EXAMPLE 12

Figure 5:
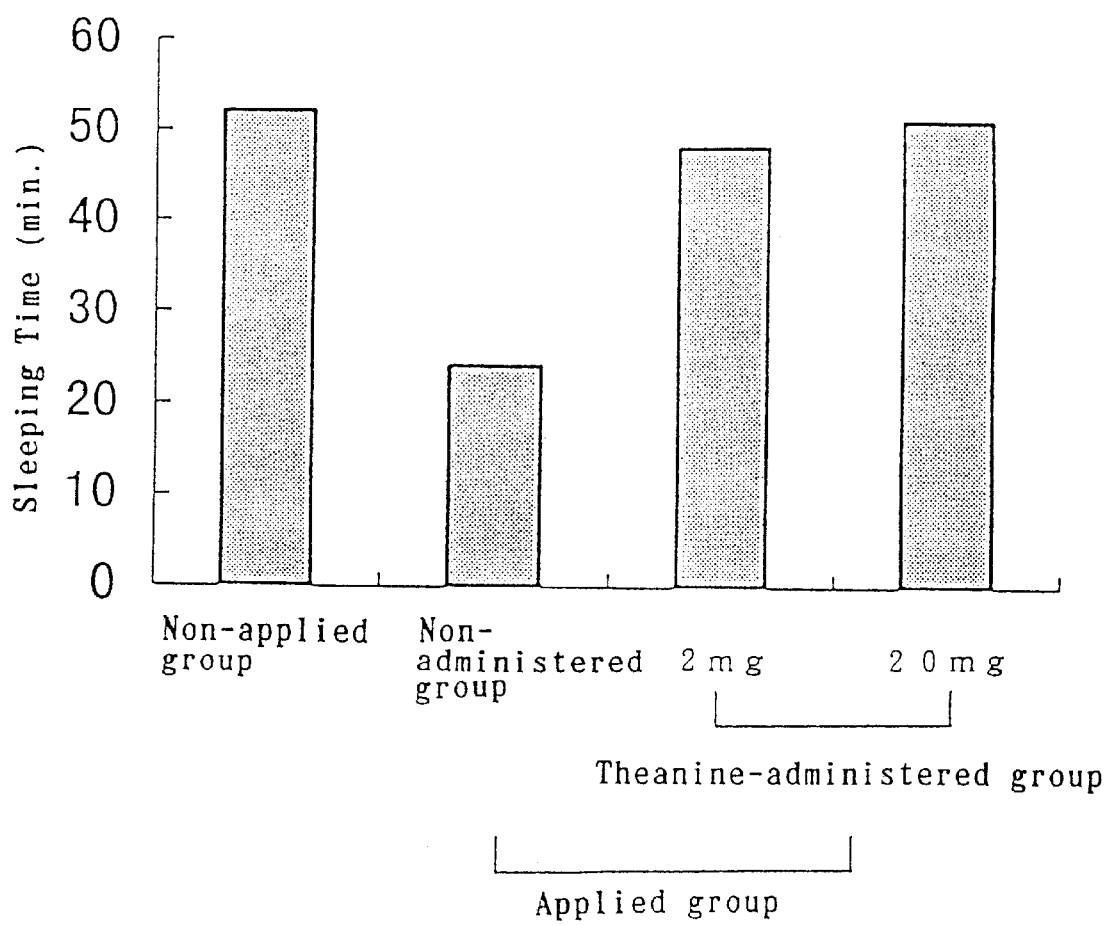
FIG. 5 is a graph showing sleeping time for theanine-administered group, non-applying group, and non-administered group, respectively.

To 10 week-old ovariectomized rats (7 rats/group) was applied a foot shock electric stress (0.3 mA) once a day. In addition, one hour before applying the electric stress, the rats were orally administered with 2 mg or 20 mg of theanine per 1 kg of body weight in the form of an aqueous solution by using a probe. The rats of the control group were administered with 1 ml of water by using a probe. Such an electric shock was applied to rats for 7 days. On the day following the final electric stress-applying day, sodium pentobarbital was intraperitoneally administered in an amount of 50 mg/kg, and the sleeping time was measured. The results for the theanine-administered group, the non-applied group, and non-administered group are respectively shown in FIG. 5.

It could be confirmed that the sleep disorders in menopause was suppressed by the administration of the theanine composition.

EXAMPLE 13

Two-hundred and thirty-one women patients diagnosed as menopausal disorders took one theanine-containing capsule (200 mg/capsule) per day. The dose period was set to be 28 days. The degree of improvement in the menopausal disorders were evaluated by doctors and patients, respectively. The results are shown in Tables 11 and 12.

TABLE 11

(Judgment by Patients)

| Impression of Patients | Response Ratio (%) |
| --- | --- |
| Excellent | 25.1 |
| Good | 68.4 |
| No changes | 6.5 |
| Worse | 0 |
| Level of not less than "good" | 93.5 |

TABLE 12

(Judgment by Doctors)

| Impression of Doctors | Response Ratio (%) |
| --- | --- |
| Remarkable Effect | 13.9 |
| Effect | 42.0 |
| Slight Effect | 38.1 |
| No changes | 6.1 |
| Worse | 0.0 |
| Level of not less than "effect" | 55.8 |
| Level of not less than "slight effect" | 93.9 |

EQUIVALENTS

Those skilled in the art will be able to recognize or ascertain, many equivalents to the specific embodiments of the invention described in the present specification by using simple routine experimentation. Such equivalents are intended to be encompassed in the scope of the following claims.

INDUSTRIAL APPLICABILITY

The theanine-containing composition of the present invention has effects of suppression or amelioration to a plurality of the kinds of diseases, specifically to symptoms accompanying diminished homeostasis, such as obesity, anxiogenic symptoms, premenstrual syndrome, sensitivity to cold, menopausal disorders, sleep disorders and autonomic imbalance. Moreover, since the composition of the present invention comprises theanine as an active ingredient, its safety is high, and the composition is administered easily. In addition, the mineral composition of the present invention has a reduced peculiar metal taste, and the intake of the minerals can be made easily by the use of the inventive product.

What is claimed is:

1. A method for reducing metal taste of a mineral composition wherein one or more minerals are present in an amount sufficient to cause metal taste, comprising:

adding purified theanine to the mineral composition in an amount sufficient to reduce metal taste of the mineral composition.

2. The method according to claim 1, wherein the mineral is selected from the group consisting of iron, magnesium, copper, zinc, selenium, calcium, potassium, manganese, chromium, iodine, molybdenum, nickel, vanadium and salts thereof.

3. The method according to claim 1, wherein said metal taste is selected from the group consisting of astringent taste, bitter taste, sour taste, salty taste, pungent taste, puckery taste and hot taste.

4. The method according to claim 1, further comprising:

reducing metal content of the mineral composition.

* * * * *